United States Patent [19]

Lin

[11] Patent Number: 4,484,002

[45] Date of Patent: Nov. 20, 1984

[54] PROCESS FOR PRODUCING METHYL ACETATE FROM METHANOL AND CARBON MONOXIDE USING A NOVEL CATALYST SYSTEM

[75] Inventor: Jiang-Jen Lin, Round Rock, Tex.

[73] Assignee: Texaco Inc., White Plains, N.Y.

[21] Appl. No.: 339,236

[22] Filed: Jan. 13, 1982

[51] Int. Cl.$^3$ .................... C07C 67/36; C07C 69/14
[52] U.S. Cl. ..................... 560/232; 502/153; 502/154; 502/155; 502/161; 502/164; 562/519
[58] Field of Search ................ 560/232, 204; 260/410.9 R; 562/519; 252/428, 429 R, 430, 431 R, 431 N, 431 P; 502/153–155, 161, 164

[56] References Cited

U.S. PATENT DOCUMENTS 3,769,324 10/1973 Paulik et al. .................. 560/232
3,856,856 12/1974 Nozaki ........................ 560/232

*Primary Examiner*—Vivian Garner
*Attorney, Agent, or Firm*—Jack H. Park; Cynthia L. Kendrick

[57] ABSTRACT

Methyl acetate is prepared in good yield by reacting methanol with carbon monoxide in the presence of a homogeneous catalyst composition comprising a ruthenium-containing compound, a cobalt-containing compound and a quaternary onium salt or base, and heating the resulting mixture at an elevated temperature and pressure for sufficient time to produce the desired methyl acetate, and then recovering the same from the reaction mixture.

18 Claims, No Drawings

PROCESS FOR PRODUCING METHYL ACETATE FROM METHANOL AND CARBON MONOXIDE USING A NOVEL CATALYST SYSTEM

BACKGROUND OF THE INVENTION

1. Field of the Invention

This invention relates to a new process for preparing methyl acetate. More particularly, the invention relates to an improved process for preparing methyl acetate from methanol and carbon monoxide using a novel catalyst system.

Specifically, the invention provides a new and improved process for preparing methyl acetate in good yield from methanol and carbon monoxide which process comprises contacting a mixture of methanol and carbon monoxide with a catalyst composition comprising a ruthenium-containing compound, a cobalt-containing compound and a quaternary onium base or salt, and heating the resulting mixture at an elevated temperature and pressure for sufficient time to produce the desired methyl acetate, and then recovering the same from the reaction mixture.

2. Prior Art

Methyl acetate is a chemical which has found wide use in industry. It is used, for example, in the production of acetic acid anhydride, acetic acid, and ethyl acetate, and as a solvent or diluent.

Various methods have been used in the past for the production of the methyl acetate. This ester can be produced, for example, by the reaction of methyl alcohol with acetic acid which in turn is obtained by carbonylation using rhodium and iodine promoter. A direct synthesis from methyl alcohol would be more economical and highly desirable.

It has been proposed to prepare the methyl acetate by the direct carbonylation of methanol, but these methods up to the present have not been entirely satisfactory as they give low yields of the desired ester or use expensive catalysts or catalysts that are difficult to utilize on a large scale. For example, Paulik et al-Chem. Communications, 1578 (1968) disclose the carbonylation of methanol using a rhodium compound and an iodide promoter. The chief product in this case, however, is acetic acid rather than the desired methyl acetate. U.S. Pat. No. 2,729,651, U.S. Pat. No. 2,727,902, and German Pat. Nos. 933,148, 921,938 and 947,460 disclose other methods for carbonylation of methanol using various nickel and cobalt catalysts, but again the yields of the desired methyl acetate are low. British patent applications Nos. 2,007,212A, 2,009,172A and 2,007,658A disclose methods for carbonylation of methanol using catalyst systems containing an iodine promoter. The yields are again low and in addition the processes utilize the iodine promoters that are corrosive material and difficult to utilize on a large scale.

It is an object of the invention, therefore, to provide a new and improved process for preparing methyl acetate. It is a further object to provide a process for preparing methyl acetate from methanol using a new and improved catalyst system. It is a further object to provide a new process for making methyl acetate from methanol which gives improved selectivity and yield. It is further object to provide a new process for making methyl acetate from methanol which avoids the use of iodine and other type promoters that are corrosive and difficult to use on a large scale. Other objects and advantages of the invention will be apparent from the following description thereof.

SUMMARY OF THE INVENTION

It has now been discovered that these and other objects may be accomplished by the process of the invention comprising contacting a mixture of methanol and carbon monoxide with a catalyst composition comprising a ruthenium-containing compound, such as ruthenium oxide, a cobalt-containing compound, such as dicobalt octacarbonyl, and a quaternary onium base or salt, such as tetra-n-butylphosphonium bromide, and heating the resulting mixture at an elevated temperature and pressure for sufficient time to produce the desired methyl acetate, and then recovering the same from the reaction mixture. It was surprising to find that this new catalyst system is highly selective for the formation of methyl acetate with high conversion rates for the methanol. A further advantage of the process being that it avoids the use of iodine and other promoters which are difficult to utilize in large scale commercial operations.

The process of the invention is particularly characterized by the high selectivity in the conversion of the methanol to methyl acetate according to the equation:

$$2CH_3OH + CO \rightarrow CH_3COOCH_3 + H_2O \qquad (1)$$

Typical conversion of methanol range from 70% to about 100%, with selectivities of methyl acetate ranging from 60% to 90%. Valuable by-products of the reaction include ethyl acetate and acetic acid.

DETAILED DESCRIPTION OF THE INVENTION

In the operation of the process of the invention, the methyl acetate, along with minor by-products such as acetic acid and ethyl acetate, are produced concurrently from methanol and carbon monoxide by a process comprising the following steps:

(1) contacting a mixture of the methanol and carbon monoxide with a catalyst comprising a ruthenium-containing compound, a cobalt-containing compound and a quaternary onium salt or base, said reaction mixture preferably containing a solvent, such as dioxane, (b) heating the said mixture to an elevated temperature, e.g. above 150° C., and an elevated pressure, e.g. above 500 psi, with sufficient carbon monoxide to satisfy the stoichiometry of the desired methyl acetate synthesis, until substantial formation of the desired ester has been achieved, and, (c) preferably isolating the said methyl acetate and minor by-products from the reaction mixture, as by distillation.

In order to present the inventive concept of the present invention in the greatest possible detail, the following supplementary disclosure is submitted. The process of the invention is practiced as follows:

As noted, the new catalyst system used in the process of the invention contains a ruthenium-containing compound, a cobalt-containing compound and a quaternary onium salt or base. The ruthenium-containing compounds employed as a catalyst may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) iodide, tricarbonyl ruthenium nitrate, or as the salt of a suitable organic carboxylic acid, for example, ruthenium(III) acetate, ruthenium naphthenate, ruthenium valerate and ruthenium complexes with carbonyl-containing ligands such as ruthenium(III) acetylacetonate. The ruthenium may also be added to the reaction zone as a carbonyl or hydrocarbonyl derivative. Here, suitable examples include, among others, triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $(Ru(CO)_3Cl_2)_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium propionate, ruthenium(III) acetylacetonate, and triruthenium dodecacarbonyl.

The cobalt-containing compound to be used in the catalyst composition may take many different forms. For instance, the cobalt may be added to the reaction mixture in the form of an oxide, salt, carbonyl derivative and the like. Examples of these include, among others, cobalt oxides $Co_2O_3$, $Co_3O_4$, $CoO$, cobalt(II) bromide, cobalt(II) iodide, cobalt(II) thiocyanate, cobalt(II) hydroxide, cobalt(II) carbonate, cobalt(II) nitrate, cobalt(II) phosphate, cobalt acetate, cobalt naphthenate, cobalt benzoate, cobalt valerate, cobalt cyclohexanoate, cobalt carbonyls, such as dicobalt octacarbonyl $Co_2(CO)_8$, tetracobalt dodecacarbonyl $Co_4(CO)_{12}$ and hexacobalt octadecacarbonyl $Co_6(CO)_{18}$ and derivatives thereof by reaction with ligands, and preferably group V donors, such as the phosphines, arsines and stibine derivatives such as $(Co(CO)_3L)_2$ wherein L is $PR_3$, $AsR_3$ and $SbR_3$ wherein R is a hydrocarbon radical, cobalt carbonyl hydrides, cobalt carbonyl halides, cobalt nitrosyl carbonyls as $CoNO(CO)_3$, $Co(NO)(CO)_2PPh_3$, cobalt nitrosyl halides, organometallic compounds obtained by reacting cobalt carbonyls with olefins, allyl and acetylene compounds, such as bis($\pi$-cyclopentadienyl) cobalt $(\pi C_5H_5)_2Co$, cyclopentadienyl cobalt dicarbonyl, bis(hexamethylene-benzene)cobalt.

Preferred cobalt-containing compounds to be used in the catalyst system comprise those having at least one cobalt atom attached to carbon, such as the cobalt carbonyls and their derivatives as, for example, dicobalt octacarbonyl, tetracobalt dodecacarbonyl, $(Co(CO)_3P(CH_3)_3)_2$, organometallic compounds obtained by reacting the cobalt carbonyls with olefins, cycloolefins, allyl and acetylene compounds such as cyclopentadienyl cobalt dicarbonyl, cobalt carbonyl halides, cobalt carbonyl hydrides, cobalt nitrosyl carbonyls, and the like, and mixtures thereof.

Particularly preferred cobalt-containing compounds to be used in the catalyst comprise those having at least one cobalt atom attached to at least three separate carbon atoms, such as for example, the dicobalt octacarbonyls and their derivatives.

The quaternary onium salt or base to be used in the catalyst composition may be any onium salt or base, but are preferably those containing phosphorous or nitrogen, such as those of the formula

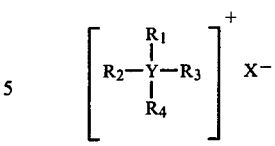

wherein Y is phosphorous or nitrogen, $R_1$, $R_2$, $R_3$ and $R_4$ are organic radicals preferably alkyl, aryl or alkaryl radicals, and X is an anionic species. The organic radicals useful in this instance include those alkyl radicals having from 1 to 20 carbon atoms in a branched or linear alkyl chain, such as methyl, ethyl, n-butyl, isobutyl, octyl, 2-ethylhexyl and dodecyl radicals. Tetraethylphosphonium bromide and tetrabutylphosphonium bromide are typical examples presently in commercial production. The corresponding quaternary phosphonium or ammonium acetates, hydroxides, nitrates, chromates, tetrafluoroborates and other halides, such as the corresponding chlorides, and iodides, are also satisfactory.

Equally useful are the phosphonium and ammonium salts containing phosphorous or nitrogen bonded to a mixture of alkyl, aryl and alkaryl radicals, which radicals preferably contain from 6 to 20 carbon atoms. The aryl radical is most commonly phenyl. The alkaryl group may comprise phenyl substituted with one or more $C_1$ to $C_{10}$ alkyl substituents, bonded to phosphorous or nitrogen through the aryl function.

Illustrative examples of suitable quaternary onium salts or bases include tetrabutylphosphonium bromide, heptyltriphenylphosphonium bromide, tetrabutylphosphonium iodide, tetrabutylammonium chloride, tetrabutyl phosphonium nitrate, tetraoctylphosphonium hydroxide, tetrabutylphosphonium chromate, tetraoctylphosphonium tetrafluoroborate, tetrahexyl phosphonium acetate and tetraoctylammonium bromide. The onium salt can be a tetrahydrocarbylphosphonium salt.

The preferred quaternary onium salts and bases to be used in the process comprise the tetralkylphosphonium salts containing alkyl groups having 1 to 6 carbon atoms, such as methyl, ethyl, butyl, hexyl, heptyl and isobutyl. Tetralkylphosphonium salts, such as the halides, bromides, chlorides and iodides, and the acetate and chromate salts and hydroxide base, are the most preferred.

The quantity of the ruthenium-containing compound and the cobalt-containing compound to be used in the process of the invention may vary over a wide range. The process is conducted in the presence of a catalytically effective quantity of the active ruthenium-containing compound and the active cobalt-containing compound which gives the desired product in a reasonable yield. The reaction proceeds when employing as little as about $1 \times 10^{-6}$ weight percent, and even lesser amounts of the ruthenium-containing compound, together with as little as about $1 \times 10^{-6}$ weight percent of the cobalt-containing compound, or even lesser amounts, based on the total weight of the reaction mixture. The upper concentration is dictated by a variety of factors including catalyst cost, partial pressures of carbon monoxide, operating temperature, etc. A ruthenium-containing compound concentration of from about $1 \times 10^{-5}$ to about 10 weight percent in conjunction with a cobalt-containing compound concentration of from about $1 \times 10^{-5}$ to about 5 percent, based on the total weight of the reaction mixture is generally desirable in the practice of this invention. The preferred ruthenium to cobalt atomic ratios are from about 10:1 to 1:10.

Generally, in the catalyst system used in the process of the invention, the molar ratio of the ruthenium-containing compound to the quaternary onium salt or base will range from about 1:1.01 to about 1:100 or more, and preferably will be from about 1:1.5 to about 1:20.

Particularly superior results are obtained when the above-noted three components of the catalyst system are combined in a molar basis as follows: ruthenium-containing compound 0.1 to 4 moles, cobalt-containing compound 0.025 to 1.0 moles, and the quaternary 0.4 to 60 moles, and still more preferably when the components are combined in the following molar ratios: ruthenium-containing compound 1 to 4 moles, cobalt-containing compound 0.25 to 1.0 moles and the quaternary onium base or salt 10 to 50 moles.

Solvents may be and preferably are employed in the process of the invention. Suitable solvents for the process include the oxygenated hydrocarbons, e.g. compounds composed only of carbon, hydrogen and oxygen and one in which the oxygen atom present is in an ether, ester, ketone carbonyl or hydroxyl group or groups. Generally, the oxygenated hydrocarbon will contain from about 3 to 12 carbon atoms and preferably a maximum of three oxygen atoms. The solvent must be substantially inert under the reaction conditions, must be relatively non-polar and must be one which has a normal boiling point of at least 65° C. at atmospheric pressure and preferably, the solvent will have a boiling point greater than that of the methyl acetate and other products of the reaction so that recovery of the solvent by distillation is facilitated.

Preferred ester type solvents are the aliphatic, cycloaliphatic and aromatic carboxylic acid esters as exemplified by methyl benzoate, isopropyl benzoate, butyl cyclohexanoate, as well as dimethyl adipate. Useful alcohol-type solvents include monohydric alcohols as cyclohexanol and 2-octanol, etc. Suitable ketone-type solvents include, for example, cyclic ketones such as cyclohexanone, 2-methylcyclohexanone, as well as acyclic ketones, such as 2-pentanone, butanone, acetophenone, etc. Ethers which may be utilized as solvents include cyclic, acyclic, and heterocyclic materials. Preferred ethers are the heterocyclic ethers as illustrated by 1,4-dioxane and 1,3-dioxane. Other suitable ethers include isopropyl propyl ether, diethylene glycol dibutyl ether, dibutyl ether, ethyl octyl ether, diphenyl ether, heptyl phenyl ether, anisole, tetrahydrofurane, etc. The most useful solvents of all of the above groups include the ethers as represented by monocyclic, heterocyclic ethers, such as 1,4-dioxane, etc.

The amount of the solvent employed may vary as desired. In general, it is desirable to use sufficient solvent to fluidize the catalyst system. In general, this may vary from about 0.5 mol to 2 mol per mol of ruthenium.

The temperature range which can usefully be employed in the process of the invention may vary over a considerable range depending upon experimental factors, including the choice of catalyst, pressure and other variables. The preferred temperatures are above 100° C., and more preferably between 150° C. and 350° C. when super-atmospheric pressures of the carbon monoxide are employed. Coming under special consideration are the temperatures ranging from about 180° C. to about 250° C.

Superatmospheric pressures of 500 psi or greater lead to substantial yield of the desired ester. A preferred operating range is from about 1000 psi to about 7500 psi, although pressures above 7500 psi also provide useful yields of the desired product. The pressures referred to herein represent the total pressure generated by all the reactants, although they are substantially due to the carbon monoxide reactant.

The relative amounts of carbon monoxide which may be initially present in the reaction mixture may vary over a considerable range. In general, the amount of the carbon monoxide should be at least sufficient to satisfy the stoichiometry of the reaction with the methanol to form the methyl acetate. Excess carbon monoxide is preferably employed in conjunction with maintaining the pressure as noted above. Particularly in continuous operations, but also in batch experiments, the carbon monoxide may also be used in conjunction with up to 50% by volume of one or more other gases. These other gases may include one or more inert gases, such as nitrogen, argon, neon and the like, or they may include gases that may, or may not undergo reaction under the conditions of the present process, such as hydrocarbons, such as methane, ethane, propane, and the like, ethers such as dimethyl ether, methylethyl ether, and diethyl ether, and higher alcohols.

The desired product of the reaction, methyl acetate, will be formed in significant quantities varying from about 60% to about 90% selectivities. Also formed will be minor by-products, such as ethyl acetate and acetic acid and minor amounts of other oxygenated products. The desired products can be recovered from the reaction mixture by conventional means, such as fractional distillation in vacuo, etc.

The process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired methyl acetate product, and said material can be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), infrared (ir) mass spectometry, nuclear magnetic reasonance (nmr) and elemental analyses, or a combination of these techniques. Analyses have, for the most part, being by parts by weight; all temperatures are in degree centigrade and all pressures in pounds per square inch (psi).

To illustrate the process of the invention, the following examples are given. It is to be understood, however, that the examples are given in the way of illustration and are not to be regarded as limiting the invention in any way.

EXAMPLE I

This example illustrates the high selectivity of the new catalyst system in the production of methyl acetate from methanol.

A glass liner was charged with ruthenium dioxide hydrate, (2.0 mmole), tetra-n-butylphosphonium bromide (20 mmoles) and dicobalt octacarbonyl (4 mmoles) and 16 g of methanol and 10 g of p-dioxane added thereto. The glass liner was placed in a stainless steel reactor and purged of air with carbon monoxide, then pressured to about 2000 psi with carbon monoxide and the mixture heated to 169° C. The maximum pressure, 3375 psi, was observed after one heating process. After 18 hours at 169° C., the reactor was allowed to cool, the gas pressure noted, (1800 psi) the excess gas vented and the liquid product recovered (35.2 g).

The liquid product was analyzed by glc and the selectivities of products were calculated to be
90% by weight of methyl acetate
5% by weight of ethyl acetate
There was a 56% conversion of the methanol.

The above results are surprising in view of the results obtained by the use of related catalyst systems in the same process.

For example, the procedure of Example I was repeated with the exception that the catalyst consisted of only 1 mmole of dicobalt octacarbonyl and no ruthenium component was used. Temperature was maintained at 200° C. and the pressure at 6115 psi. At the end of 18 hours, no methyl acetate had been detected.

EXAMPLE II

Example I was repeated by using essentially the same catalyst consisting of 2 mmole ruthenium dioxide hydrate, 4 mmole dicobalt octacarbonyl, 20 mmoles of tetra-n-butylphosphonium bromide. The mixture was kept at higher temperature, 180° C. and 3500 psi of maximum pressure for 18 hours. Analysis of the resulting liquid product and the calculated product selectivity were:
83% by weight of methyl acetate
9% by weight of ethyl acetate
There was a 95% conversion of the methanol.

EXAMPLE III

The procedure of Example I was repeated with the exception that the catalyst consisted of the following: 3 mmole ruthenium dioxide hydrate, 3 mmole dicobalt octacarbonyl and 30 mmole of tetra-butylphosphonium bromide. 24 g of methanol was utilized and no solvent was used. The mixture was heated at 195° C. and pressure of 3280 for a reaction period of 5 hours. Analysis of the resulting liquid product was as follows:
76% by weight methyl acetate
2% by weight acetic acid
6% by weight ethyl acetate
There was a 54% conversion of the methanol.

EXAMPLE IV

The procedure of Example I was repeated with the exception that the catalyst consisted of the following: 2 mmole ruthenium dioxide hydrate, 0.5 mmole dicobalt octacarbonyl, 20 mmole tetra-n-butylphosphonium bromide. 16 g of methanol was utilized along with 40 g of p-dioxane and 20 g of diethylene glycol. The temperature was maintained at 200° C. and the pressure at 3500 psi. At the end of 18 hours, the mixture was cooled and the liquid product analyzed. The product selectivities were calculated to be the following:
61% by weight of methyl acetate
4% by weight acetic acid
7% by weight ethyl acetate
There was a 46% conversion of the methanol.

EXAMPLE V

Example I was repeated with the exception that the catalyst consisted of the following: 2 mmole ruthenium dioxide hydrate, 0.5 mmole dicobalt octacarbonyl, 20 mmole tetra-n-butylphosphonium bromide. 16 g of methanol and 50 g of p-dioxane were added. The reaction was maintained at 200° C. and 3585 psi pressure. Analysis of the resulting liquid product was:
68% by weight methyl acetate
2% by weight acetic acid
10% by weight ethyl acetate
There was a 57% conversion of the methanol.

EXAMPLE VI

The procedure of Example I was repeated with the exception that the catalyst consisted of the following: 1 mmole ruthenium dioxide hydrate, 1 mmole of dicobalt octacarbonyl, 10 mmole of tetra-n-butylphosphonium bromide. 8 g of methanol was used without any solvent. The temperature was maintained at 200° C. and the pressure at 3515 psi. Analysis of the resulting liquid product was:
69% by weight methyl acetate
8% by weight acetic acid
2% by weight propyl acetate
8% by weight ethyl acetate
Conversion of methanol was 89%.

EXAMPLE VII

The procedure of Example I was repeated with the exception that the catalyst consisted of the following: 2 mmole ruthenium dioxide hydrate, 4 mmole dicobalt octacarbonyl, 20 mmole of tetra-n-butylphosphonium bromide. 16 g of methanol and 10 g of p-dioxane was added. The temperature was maintained at 198° C. and pressure at 3740 psi. Analysis of the liquid product was as follows:
45% methyl acetate
28% acetic acid
19% ethyl acetate
There was a 99% conversion of the methanol.

EXAMPLE VIII

The procedure of Example I was repeated with the exception that the catalyst consisted of the following: 2.5 mmole ruthenium dioxide hydrate, 10 mmole dicobalt octacarbonyl, 25 mmole tetra-n-butylphosphonium bromide. 40 g of methanol and 25 g of p-dioxane were utilized. Temperature was maintained at 200° C. and the pressure at 2700 psi. Analysis of the resulting liquid product was:
50% by weight methyl acetate
15% by weight ethyl acetate
2% by weight propyl acetate
2% by weight butyl acetate
There was a 34% conversion of the methanol.

EXAMPLE IX

The procedure of Example I was repeated with the exception that the catalyst consisted of: 3 mmole ruthenium dioxide hydrate, 3 mmole dicobalt octacarbonyl, 30 mmole tetra-n-butylphosphonium bromide. 24 g of methanol and 30 g of p-dioxane were added. The temperature was maintained at 230° C. for 4 hours (3630 psi pressure). Analysis of the resulting liquid product was:
68% by weight methyl acetate
11% by weight of ethyl acetate
Conversion of methanol was 73%.

EXAMPLE X

Examples I to IX are repeated with the exception that the ruthenium dioxide is replaced with an equivalent amount of triruthenium dodecacarbonyl. Related results are obtained.

EXAMPLE XI

Examples I to IX are repeated with the exception that the dicobalt octacarbonyl is replaced with an equivalent amount of Cobalt(II) acetate. Related results are obtained.

EXAMPLE XII

Examples I to IX are repeated with the exception that the tetra-n-butylphosphonium bromide is replaced with an equivalent amount of methyltriphenylphosphonium bromide. Related results are obtained.

What is claimed is:

1. A process for preparing methyl acetate from methanol and carbon monoxide which comprises contacting a mixture of methanol and carbon monoxide with a catalytic amount of an iodide-free catalyst system which comprises an iodide-free ruthenium-containing compound, an iodide-free cobalt-containing compound and an iodide-free quaternary onium salt or base, heating the resulting mixture at a temperature above 100° C. and a superatmospheric pressure for sufficient time to produce the desired methyl acetate, and then recovering the same from the reaction mixture.

2. A process as in claim 1 wherein the said reaction mixture is heated at a temperature of from 150° C. to 350° C.

3. A process as in claim 1 wherein the process is conducted at a pressure between about 1000 psi and 7500 psi.

4. A process as in claim 1 wherein the ruthenium-containing compound is a member of the group consisting of oxides of ruthenium, ruthenium acetylacetonate, and ruthenium carbonyl and hydrocarbonyl compounds.

5. A process as in claim 1 wherein the ruthenium-containing compound is a member of the group consisting of anhydrous ruthenium(IV) dioxide, ruthenium (IV) dioxide hydrate, ruthenium(VIII) tetraoxide, ruthenium acetate, ruthenium propionate, ruthenium(III) acetylacetonate, and triruthenium dodecacarbonyl.

6. A process as in claim 1 wherein the cobalt-containing compound is a member of the group consisting of cobalt carbonyls and derivatives thereof obtained by reacting the carbonyls with a group V donor ligand, cobalt carbonyl hydrides, cobalt carbonyl halides, cobalt nitrosyl carbonyls, cycloalkadienyl cobalt carbonyls, cobalt halides, cobalt oxides, and cobalt salts of organic carboxylic acids.

7. A process as in claim 1 wherein the quaternary onium salt or base is a quaternary phosphonium salt.

8. A process as in claim 1 wherein the quaternary onium salt or base is a quaternary ammonium salt.

9. A process as in claim 1 wherein the quaternary onium salt or base is a tetrahydrocarbyl phosphonium salt.

10. A process as in claim 1 wherein the quaternary onium salt or base is a tetralkylphosphonium salt.

11. A process as in claim 10 wherein the tetralkylphosphonium salt is selected from the group consisting of tetralkylphosphonium bromides, chlorides, and chromates.

12. A process as in claim 1 wherein an oxygen-containing solvent is included in the reaction mixture.

13. A process as in claim 12 wherein the solvent is a dioxane.

14. A process as in claim 1 wherein the catalyst components are utilized in the following molar ratios: ruthenium-containing compound 0.1 to 4 moles; cobalt-containing compound 0.025 to 1.0 moles; quaternary onium salt or base 0.4 to 60 moles.

15. A process as in claim 1 wherein the ruthenium-containing compound is ruthenium dioxide hydrate.

16. A process as in claim 1 wherein the cobalt-containing compound is dicobalt octacarbonyl.

17. A process as in claim 1 wherein the quaternary onium salt or base is tetrabutylphosphonium bromide.

18. A process for preparing methyl acetate which comprises reacting methanol with carbon monoxide in the presence of an iodide-free catalyst system which comprises ruthenium oxide, a cobalt carbonyl and an iodide-free quaternary phosphonium salt at a temperature above 150° C. and superatmospheric pressure until the desired methyl acetate is formed and then recovering the same.

* * * * *